(12) United States Patent
Emmerich

(10) Patent No.: US 9,023,044 B2
(45) Date of Patent: May 5, 2015

(54) ELECTROSURGICAL INSTRUMENT

(75) Inventor: Bernd Emmerich, Emmingen (DE)

(73) Assignee: Karl Storz GmbH & Co. KG (DE)

( * ) Notice: Subject to any disclaimer, the term of this patent is extended or adjusted under 35 U.S.C. 154(b) by 288 days.

(21) Appl. No.: 13/469,776

(22) Filed: May 11, 2012

(65) Prior Publication Data

US 2012/0289957 A1 Nov. 15, 2012

(30) Foreign Application Priority Data

May 13, 2011 (DE) .......................... 10 2011 075 781

(51) Int. Cl.
*A61B 18/14* (2006.01)
*A61B 17/29* (2006.01)
*A61B 18/00* (2006.01)

(52) U.S. Cl.
CPC ..... *A61B 18/1445* (2013.01); *A61B 2017/2929* (2013.01); *A61B 2018/00202* (2013.01); *A61B 2018/00607* (2013.01); *A61B 2018/00952* (2013.01)

(58) Field of Classification Search
CPC ............... A61B 2018/1442; A61B 2018/1457; A61B 2018/146; A61B 18/1442; A61B 18/1445; A61B 18/1447
USPC ...................................... 606/50–52, 205–211
See application file for complete search history.

(56) References Cited

U.S. PATENT DOCUMENTS 5,810,805 A 9/1998 Sutcu et al.
6,273,887 B1 8/2001 Yamauchi et al.

FOREIGN PATENT DOCUMENTS

| DE | 102005013871 A1 | 10/2005 |
|---|---|---|
| DE | 102004026179 A1 | 12/2005 |
| EP | 0795301 A1 | 9/1997 |
| EP | 1681027 A1 | 7/2006 |
| EP | 2042113 A1 | 4/2009 |

OTHER PUBLICATIONS

German Search Report; Application No. DE 10 2011 075 781.3; Issued: Dec. 1, 2011; 4 pages.
European Search Report; Application No. EP 12 00 3421; Issued: Aug. 6, 2012; Mailing Date: Aug. 13, 2012; 6 pages.
European Patent Office English Translation—Communication under Rule 71 (3) EPÜ—Intention to Grant Application No. 12003421.0-1659 Aug. 27, 2013; 6 pages.
European Patent Office Intention to Grant Application No. 12003421.0-1659 Issued: Aug. 27, 2013 5 pages.

*Primary Examiner* — Jaymi Della
(74) *Attorney, Agent, or Firm* — St. Onge Steward Johnston & Reens LLC

(57) ABSTRACT

An electrosurgical instrument includes a first jaw member with a first electrode area and a second electrode area and a second jaw member, such that at least either the first jaw member or the second jaw member can be pivoted around a pivot axis in such a way that the jaw members can be approached to one another or distanced from one another, so that the first jaw member can be rotated in relation to the second jaw member around a rotation axis between a first predetermined working position and a second predetermined working position, so that in the first working position the first electrode area of the first jaw member is facing the second jaw member and so that in the second working position the second electrode area of the first jaw member is facing the second jaw member.

10 Claims, 4 Drawing Sheets

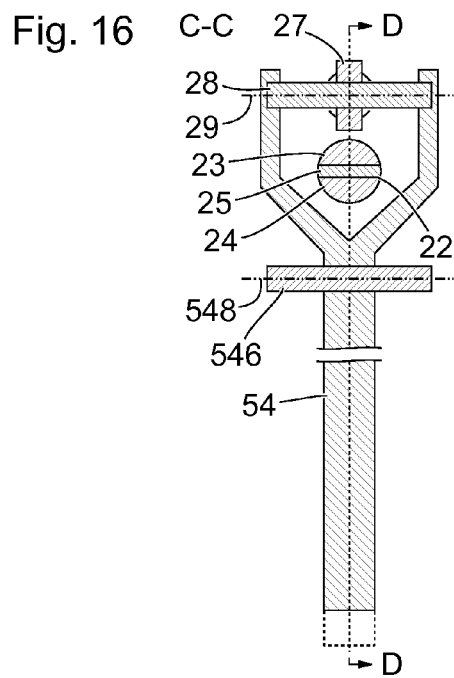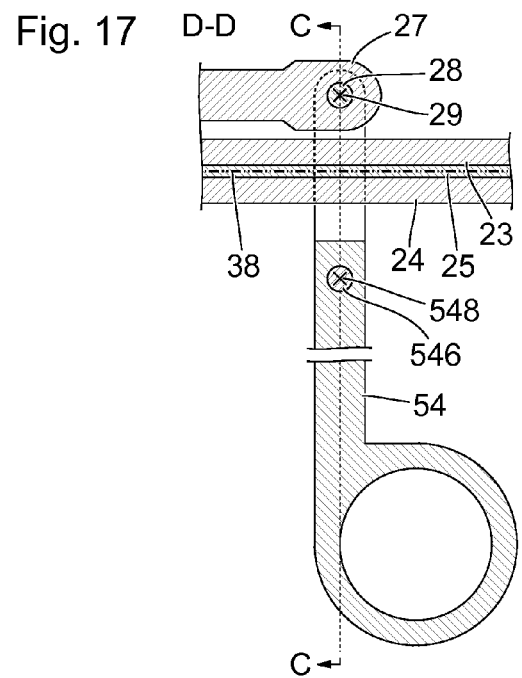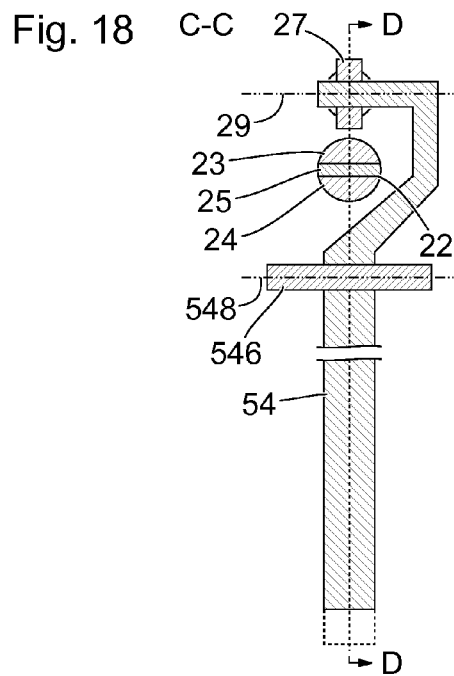

ELECTROSURGICAL INSTRUMENT

CROSS-REFERENCE TO RELATED APPLICATIONS

The present application claims priority of German Patent Application No. 10 2011 075 781.3 filed on May 13, 2011, the content of which is incorporated herein by reference.

FIELD OF THE INVENTION

The present invention relates to an electrosurgical instrument and a method for preparing an electrosurgical procedure.

BACKGROUND OF THE INVENTION

In electrosurgery or in electrosurgical procedures, (Joulean) heat is generated in tissue by the flow of electric current and on the basis of electrical resistance of tissue. As a result of the shape and arrangement of electrodes that are used in this process, the flow of current is localized as precisely as possible. The tissue through which current has flowed is atrophied or destroyed by the resulting heat. As a result, tissues can be stuck together, for example, or closed, and bleeding can be stanched.

High-frequency alternating currents are used as a rule in electrosurgery in order to prevent stimulation of nerves and other undesired side effects. The terms "electrosurgery" and "HF surgery" therefore are often used synonymously. Another term often used synonymously is that of electrocauterization.

In micro-invasive and other procedures, electrosurgical methods are used to atrophy large-surface tissues in order to seal vessels in a small area or to atrophy cut surfaces as early as the cutting or immediately thereafter. For these and other applications, different current density distributions in the tissue are advantageous and desired in each case. Medical staff, particularly physicians, can influence the current density distribution by using different-shaped electrodes or tools and through the way these electrodes are used.

SUMMARY OF THE INVENTION

An object of the present invention consists in providing an improved electrosurgical instrument and an improved method for preparing an electrosurgical procedure.

This object is fulfilled through the content of the independent claims.

Refinements are indicated in the dependent claims.

An electrosurgical instrument includes a first jaw member with a first electrode area and a second electrode area and a second jaw member, such that at least either the first jaw member or the second jaw member can be pivoted around a pivot axis in such a way that the jaw members can be approached to one another and distanced from one another, in such a way that the first jaw member can rotate in relation to the second jaw member around a rotation axis between a first predetermined working position and a second predetermined working position, such that in the first working position the first electrode area of the first jaw member is turned toward the second jaw member and such that in the second working position the second electrode area of the first jaw member is turned toward the second jaw member.

The electrosurgical instrument is an instrument for electrosurgical procedures in the sense described above, in particular for electrocauterization. The second jaw member can include an electrically insulating material or an electrically insulating surface. Alternatively or in addition, the second jaw member can include an electrically conducting material or electrically conducting portions, which form electrodes and whose open surface areas form electrode areas or electrode surface areas. If the second jaw member comprises one or more electrodes and one or more electrode areas, they can be electrically insulated from the electrode areas of the first jaw member or can be connected by electrically conducting means with them.

The pivot axis around which at least either the first jaw member or the second jaw member can pivot is, in particular, perpendicular to the longitudinal axis of the electrosurgical instrument. A mechanically particularly simple and robust structure can be achieved if only the second jaw member can pivot around a pivot axis perpendicular to the longitudinal axis of the electrosurgical instrument, while the first jaw member can rotate only around the rotation axis. Alternatively, both jaw members can be pivotable around one pivot axis each, such that the pivot axes of the jaw members are, in particular, parallel to one another and perpendicular to the rotation axis and perpendicular to the longitudinal axis of the electrosurgical instrument.

The rotation axis of the first jaw member is, in particular, parallel to the longitudinal axis of the first jaw member or parallel or essentially parallel to the direction of the greatest linear extension of the first jaw member. The rotation axis of the first jaw member is thus, in particular, parallel to the longitudinal axis of the electrosurgical instrument. If the first jaw member can pivot around a pivot axis, the rotation axis of the first jaw member, in particular, is in the position of the first jaw member in which it is closest to the second jaw member, parallel to the longitudinal axis of the electrosurgical instrument.

The first predetermined working position and the second predetermined working position can be (detachably) fastened by one or more catch-lock devices on the distal end of the electrosurgical instrument and/or on the proximal end of the electrosurgical instrument. Alternatively or in addition, markings can be provided on the electrosurgical instrument that indicate to medical staff whether the first jaw member is situated in the first predetermined working position or in the second predetermined working position. The markings are, in particular, positioned on the proximal end of the electrosurgical instrument.

The first predetermined working position and the second predetermined working position are, in particular, distanced from one another by a predetermined angle. Between the first predetermined working position and the second predetermined working position and/or outside the angle area determined by the two predetermined working positions, one or more additional working positions can be foreseen. Alternatively or in addition to discrete predetermined working positions, one or more working ranges can be provided that each include a continuum of working positions.

The first electrode area and the second electrode area of the first jaw member can be connected by electrically conductive means. In particular, the first electrode area and the second electrode area are surface areas, mutually adjacent to or continuous with one another, of the same electrode or of the same electrically conductive component. Alternatively, the first electrode area and the second electrode area are surface areas, at a distance from one another, of the same electrode or of the same electrically conductive component. An electrically insulating surface area of the first jaw member can be positioned between the first electrode area and the second electrode area.

Alternatively, the first electrode area and the second electrode area are electrically insulated from one another and are formed by two different electrodes or two different electrically conductive components.

In particular, the shape of the first electrode area is distinguished from the shape of the second electrode area.

The rotation of the first jaw member between the first predetermined working position and the second predetermined working position can make it possible in a very brief period to adjust the shape of the particular electrode surface that is active or facing the second jaw member, to different data, different applications or different electrosurgical procedures and the different current density distributions desired in this process. Medical staff therefore, in many cases, are no longer obliged to replace the electrosurgical instrument for different electrosurgical procedures, but must merely rotate the first jaw member.

With an electrosurgical instrument as described here, the first electrode area, in particular, comprises a stronger curvature than the second electrode area.

For example, the first electrode area comprises a stripe- or line-shaped area of high curvature, which makes possible a strongly localized current density distribution. In particular, the first electrode area is curved in such a way that a contour of a cross-section along a plane perpendicular to the longitudinal direction of the first jaw member comprises, at least in sections, a small curvature radius. In particular, the first electrode area comprises a sharp edge. The edge can be configured as a cutting edge that simultaneously allows cutting and an electrocauterization of the cutting edges.

The second electrode area comprises, for example, a small curvature or is level or essentially level. With this geometric shape, the second electrode area allows a current density distribution that is essentially constant over a relatively large area. Thus, for example, large-surface electrocauterization becomes possible, especially electrosurgical closing or severing of a vein.

With an electrosurgical instrument as described here, in particular, the first electrode area is formed by a first electrode and the second electrode area by a second electrode, such that the first electrode and second electrode are electrically insulated from one another.

The first electrode and second electrode are electrically insulated from one another, in particular, by a ceramic or synthetic component. The electrical insulation of the two electrodes and thus of the two electrode areas allows only one of the two electrodes, and only one of the two electrode areas, to be selectively activated or included in an electric circuit. An electrosurgical effect by the respective other electrode, or by the respective other electrode area, can thereby be avoided, at least for the most part.

An electrosurgical instrument as described here includes, in addition, an electrical contact device for electrical contact merely of the first electrode, if the first jaw member happens to be in the first working position, and for electrical contact merely of the second electrode, if the first jaw member is in the second working position.

The contact device includes in particular a gliding contact or sliding contact, which, depending on the position of the first jaw member, forms an electrically conductive connection either to an electrically conductive component that is connected electrically conductively with the first electrode or is of one-piece configuration and electrically conductive, or to an electrically conductive component that is electrically conductively connected with the second electrode or is of one-piece configuration and electrically conductive. This allows an automatic selective contact or electrical activation or integration in the electrical switching circuit of the particular electrode area that is momentarily situated opposite the second jaw member. Thus, in particular, a separate switching process or another separate manipulation on an electrical switching circuit is superfluous. This can simplify the handling of the electrosurgical instrument.

The contact device is configured, in particular, to form, directly or indirectly, an electrically conductive connection between a plug-in contact or other electrical connection device and the first electrode or the second electrode. The plug-in contact or other electrical connection device is configured, in particular, for electrically conductive connection with an electrical power source by means of a cable.

The contact device is positioned, for example, on the distal or proximal end of the electrosurgical instrument. Because of the construction space required for a contact device, an arrangement on the proximal end of the electrosurgical instrument can be advantageous.

With an electrosurgical instrument as described here, the second jaw member, in addition, can comprise an electrode area that faces the first jaw member.

The second jaw member can comprise several electrode areas that can be electrically conductively connected with one another (formed, in particular, by the same electrode or the same electrically conductive component) or electrically insulated from one another. The electrode area on the second jaw member is, in particular, electrically insulated from the electrode areas on the first jaw member or not directly connected electrically conductively with them. Instead, the electrode area on the second jaw member on the one hand, and at least the electrode area on the first jaw member that is momentary facing the second jaw member on the other hand are configured on the first jaw member in order to be connected with two different poles of an electrical power source. In other words, the electrosurgical instrument is, in particular, configured for a bipolar application in which a (in particular, high-frequency alternating) current can be generated between the electrode area on the second jaw member and the electrode area on the first jaw member that is momentarily active or is facing the second jaw member. In a bipolar application of the electrosurgical instrument, a spatially especially well-defined current density distribution and thus an especially well-localized electrosurgical effect can be generated.

Alternatively, the electrosurgical instrument is foreseen and configured with or without an electrode surface on the second jaw member for an exclusive or optionally monopolar application. With a monopolar application of the electrosurgical instrument, the electric circuit can be closed by a large-surface electrode on the patient's body, which is also referred to as a passive electrode.

With an electrosurgical instrument having an electrode area on the second jaw member, a surface area of the second jaw member that is turned away from the first jaw member can be configured as electrically insulating. Thereby, an undesired or parasitic current flow in areas outside the intermediate space between the jaw members can be reduced or stopped.

With an electrosurgical instrument having an electrode area on the second jaw member, the electrode area on the second jaw member is configured, in particular, as level at least in sections or concave at least in sections. For example, the electrode area on the second jaw member comprises a groove or a notch having a V-shaped, U-shaped, trapezoidally shaped or other cross-section. The electrosurgical instrument can be configured in such a way that a stud-shaped or blade-shaped portion of an electrode area on the first jaw member can engage in the groove or notch on the second jaw member when the two jaw members assume their positions closest to one another.

An electrosurgical instrument as described here includes, in particular, a shaft on whose distal end the jaw members are positioned, a handling device with a rotation device on the proximal end of the shaft, such that the rotation device is configured for manual actuation, and a transmission device that mechanically couples the rotation device with the first jaw member to transmit at least either torque or a force from the rotation device to the first jaw member in order to rotate the first jaw member between its first working position and its second working position.

The rotation device includes, in particular, a rotary wheel that can be manually turned by medical staff. The transmission device includes, in particular, an axle to transmit torque. The rotation device and transmission device make it possible to select or exchange or adjust the working position of the first jaw member from the proximal end of the electrosurgical instrument. The distal end of the electrosurgical instrument with the two jaw members is not therefore required to be manually reachable to switch between working positions of the first jaw member. In particular when the electrosurgical instrument is configured with a long (straight or curved; rigid or flexible) shaft for micro-invasive applications, the rotation device and the transmission device can make it possible to switch rapidly between different electrode areas and different current density distributions. In so doing, the distal end of the electrosurgical instrument, for example, can remain in a hollow space in which engagement occurs by means of the electrosurgical instrument.

With an electrosurgical instrument having a rotation device and a transmission device, a catch-lock function can also be provided in order to block the first jaw member in the respective working positions by catch-locking. The catch-lock function, on the one hand, can allow medical staff a tactile confirmation on reaching a working position. On the other hand, the catch-lock function can prevent undesired rotation of the first jaw member out of a working position, by opposing a resistance moment to this rotation. Both options can improve ergonomic quality and safety in handling of the electrosurgical instrument.

Alternatively or in addition to a rotation device, it is possible to provide an electrical hollow shaft motor, an ultrasound motor, a power drive based on memory effect with a pseudo-elastic material, or other power drive in order to rotate the first jaw member between the predetermined working positions. One of the described power drives can simultaneously be configured in order to hold the first jaw member in a selected predetermined working position. If the power drive is provided on the distal end of the electrosurgical instrument, then in addition the transmission device to transmit torque or a force to the first jaw member can be dispensed with. A motorized rotation of the first jaw member between the predetermined working positions can make it possible to select the working position and thus the electrode area that is active, or facing the second jaw member, by a foot pedal switch or button, by speech command, on the basis of gestures or depending on a phase in a work flow.

An electrosurgical instrument as described here can be configured in such a way that the first jaw member can be removed in the distal direction.

If the electrosurgical instrument comprises a shaft on whose distal end the jaw members are positioned, then the first jaw member, in particular, can be removable in the distal direction by a movement parallel to the longitudinal axis of the shaft or to the local longitudinal axis of the shaft. The first jaw member's removability can simplify cleaning and sterilization of the electrosurgical instrument.

With an electrosurgical instrument having a transmission device, as described here, the first jaw member, in particular, together with the transmission device can be removed from the shaft in the distal direction.

The shared removable capacity of the first jaw member and transmission device makes possible a durable and thus robust mechanical connection between the jaw member and the transmission device. Removability in the distal direction can simplify cleaning of the electrosurgical instrument in that—contrary to removability in the opposite direction—impurities on the first jaw member are not admitted into the shaft.

An electrosurgical instrument in which the first jaw member together with the transmission device can be removed from the shaft in the distal direction, can also include a catch-lock function to lock the proximal end of the transmission device on the handling device. The catch-lock function is configured, in particular, to connect the proximal end of the transmission device detachably with the rotation device. The catch-lock function, provided between the proximal end of the transmission device and the rotation device, avoids problems concerning structural space that would have a limiting effect, for example, on the distal end of the electrosurgical instrument. In addition, in the aforementioned arrangement of the catch-lock function, an unlocking can be provided in the area of a handling device on the proximal end of the electrosurgical instrument.

With an electrosurgical instrument as described here, at least either the first electrode area of the first jaw member or the second electrode area of the first jaw member or a surface area of the second jaw member facing the first jaw member can be configured in the proximity of the pivot axis concavely in the longitudinal direction.

In the case of a concave configuration of the second jaw member in the longitudinal direction close to the pivot axis, an electrode area, in particular, is configured on the second jaw member concavely in the longitudinal direction. A configuration that is concave in the longitudinal direction is particularly relevant when a section along a plane perpendicular to the pivot axis contains a concave contour of the respective jaw member. Concave configuration of at least one jaw member close to the pivot axis can—especially with a bipolar configuration of the electrosurgical instrument—avoid or prevent an inordinately high current density, in the extreme case a short-circuit, between electrode surfaces on the jaw members, in closing or moving the jaw members toward one another.

With a method to prepare an electrosurgical procedure by means of an electrosurgical instrument with a first jaw member and a second jaw member, such that at least either the first jaw member or the second jaw member can be pivoted around a pivot axis in such a way that in so doing the jaw members can be approached to or distanced from one another, the first jaw member is rotated into a first working position, in which a first electrode area of the first jaw member is facing the second jaw member, or into a second working position, in which a second electrode area of the first jaw member is facing the second jaw member.

In particular when the first electrode area and the second electrode area have different shapes and thus are configured for different current density distributions, rotation of the first jaw member into one of the predetermined working positions can allow rapid adjustment of the current density distribution to different applications and requirements.

Before the above-described rotation step, medical staff can determine a desired shape of an electrode. On the basis of the determined desired shape, in a next step it is possible to determine which of several electrode areas on the first jaw member of the electrosurgical instrument comes closest to the desired shape, in order then to position this electrode area with respect to the second jaw member in the described rotation step. After rotation of the first jaw member and the resulting adjustment of the active electrode area to the desired shape, the electrosurgical instrument can be used in an electrosurgical procedure.

With a method for preparing an electrosurgical procedure as described here, use is made in particular of an electrosurgical instrument as described here.

BRIEF DESCRIPTION OF THE DRAWINGS

Embodiments are described in greater detail hereinafter with reference to the appended drawings, which are as follows:

FIG. 16 shows a schematic sectional depiction of a pivotable part of a handling device.

FIG. 17 shows an additional schematic sectional depiction of the pivotable part of FIG. 16.

FIG. 18 shows a schematic sectional depiction of an additional pivotable art of a handling device.

DETAILED DESCRIPTION OF THE INVENTION

Figure 1:
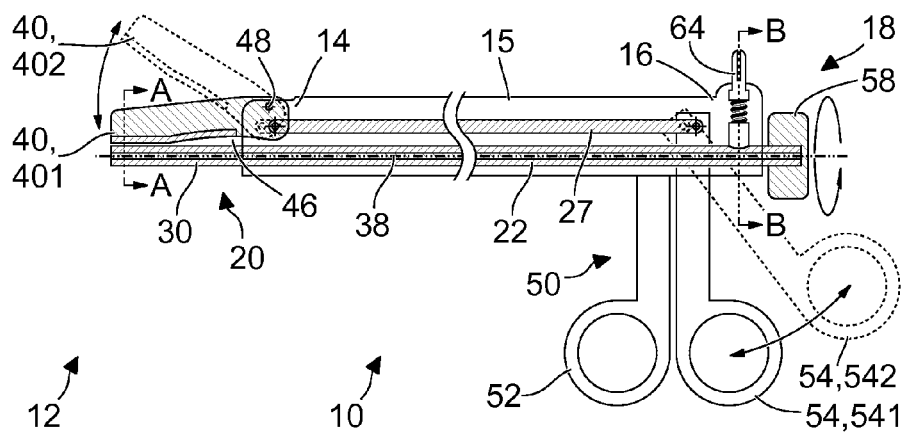
FIG. 1 shows a schematic depiction of an electrosurgical instrument.

FIG. 1 shows a schematic depiction of an electrosurgical instrument 10. FIG. 1 has, in part, the nature of a schematic sectional depiction. A few sectional surfaces are shown as hatched surfaces. Here, electrically conductive areas are hatched from below left to above right and electrically insulating areas from above left to below right. Other areas and characteristics of the electrosurgical instrument are indicated only in contours. These areas and characteristics as a rule have less significance for the functionality described hereinafter. FIG. 1 also indicates the positions of two sectional planes A-A and B-B. Sections along the sectional planes A-A and B-B are depicted in FIGS. 2 through 13 or 14 and 15.

The electrosurgical instrument 10 includes a distal end 12 and a proximal end 18. The electrosurgical instrument 10 includes a shaft 15 with a distal end 14 and a proximal end 16. The shaft can comprise an electrically insulating material or an electrically insulating coating on its outside. A tool 20 is positioned on the distal end 12 of the electrosurgical instrument 10 and detachably connected with the distal end 14 of the shaft 15 permanently or non-destructively (with or without use of the tool). The tool 20 includes a first jaw member 30 and a second jaw member 40, which can pivot around a pivot axis 48. The pivot axis 48 is perpendicular to the plane of projection of FIG. 1 and to the longitudinal axis of the electrosurgical instrument 10, in particular of the shaft 15.

The second jaw member 40 is depicted in a first, closed position 401 and—in broken lines—in a second, opened position 402. In the first, closed position 401, the jaw members 30, 40 touch one another at least in part or—as indicated in FIG. 1—are situated opposite one another in an area at a small and, in particular, constant distance.

In an area 46 close to the pivot axis 48, the surface of the second jaw member 40 situated opposite the first jaw member 30 is slightly concave in configuration. In particular, the surface of the second jaw member 40 situated opposite the first jaw member 30 in the area 46 is of concave configuration in the longitudinal direction, so that the illustrated section along a plane parallel to the longitudinal axis of the electrosurgical instrument 10 and parallel to the direction of the maximal linear extension of the second jaw member 40 comprises a concave contour. The concave area 46 can reduce the current density close to the pivot axis 48 of the second jaw member 40 in closing the jaw members 30, 40 with bipolar use of the electrosurgical instrument 10.

Positioned in the shaft 15 are an axle 22 and a pull rod 27 as transmission devices that each extend from the distal end 14 to the proximal end 16 of the shaft 15 or beyond. The axle 22 and the pull rod 27 are each, in particular, electrically conductive in configuration. Between the axle 22 and the pull rod 27, a wall can be provided for electrical insulation, although it is not shown in FIG. 1.

The axle 22 is mechanically coupled on the distal end 14 of the shaft 15 with the first jaw member 30 or, as indicated in FIG. 1, is of one-piece construction with it. The axle 22 can rotate around a rotation axis 38. Details of a structure of the axle 22 with several electrically conductive areas and with an insulating area situated in between, as well as a plug-in contact 64 that is only indicated in FIG. 1, are described below with reference to FIGS. 14 and 15. An additional plug-in contact, not shown in FIG. 1, can be provided for contacting the proximal end of the pull rod 27.

The pull rod 27 is jointedly coupled on the distal end 14 of the shaft 15 with the second jaw member 40 in such a way that sliding of the pull rod 27 in the longitudinal direction of the shaft 15 is connected with a pivot movement of the second jaw member 40 around the pivot axis 48. On the proximal end 18, the electrosurgical instrument 10 comprises a handling device 50 with a fixed part 52 and pivotable part 54. The fixed part 52 and the pivotable part 54 of the handling device 50 each comprise a bracket or loop into which one or more fingers can be inserted.

The pivotable part 54 of the handling device 50 can be pivoted between a first position 541 and a second position 542, which is shown in FIG. 1 only in broken lines. The pivotable part 54 of the handling device 50 is coupled with the proximal end of the pull rod 27 in such a way that pivoting of the pivotable part 54 between the positions 541, 542 causes a sliding of the pull rod 27 in the longitudinal direction of the shaft 15 and thus a pivoting of the second jaw member 40 around its pivot axis 48. In particular, the second jaw member 40 is situated in its first, closed position 401 when the pivotable part 54 of the handling device 50 is in its first position 541, and is in the second, open position 402 when the pivotable part 54 of the handling device 50 is in its second position 542.

The handling device 50 on the proximal end 18 of the electrosurgical instrument 10 also includes a rotation wheel 58, which is mechanically coupled with the proximal end of the axle 22, in particular mechanically rigidly connected. The rotation wheel 58, especially its mantle surface, in order to simplify manual actuation, comprises in particular a fluting or other structure that cannot be recognized in the sectional depiction in FIG. 1. A rotation of the rotation wheel 58 around the axis 38 results in a corresponding rotation of the axle 22 and of the first jaw member 30 around the same axis 38.

For catch-locking, releasable locking of the rotation wheel 58, axle 22 and first jaw member 30 in predetermined angle positions, a device is provided that is merely indicated in FIG. 1 and is described more thoroughly below with reference to FIGS. 14 and 15.

Contrary to the depiction in FIG. 1, the shaft 15 can be configured as removable from the handling device. In particular, the proximal end 16 of the shaft 15 can be inserted into a recess in the handling device 50 and can be locked by catch-locking. To release the catch-locking, a push-button, for example, can be provided on the handling device 50.

FIGS. 2 through 13 show schematic sectional depictions of various embodiments of the jaw members 30, 40. Shown in each case are sections along the planes A-A indicated in FIG. 1 that are perpendicular to the plane of projection of FIG. 1, perpendicular to the rotation axis 38 of the first jaw member 30 and perpendicular to the longitudinal axis of the shaft 15 of the electrosurgical instrument 10. In each case, two drawings with sequential numbers show the first jaw member in two different working positions 301, 302, such that the first jaw member can be shifted from one working position to the other by rotation around the rotation axis 38 (compare FIG. 1) by a predetermined angle. The rotation axis perpendicular to the illustrated sectional plane A-A is indicated in each of FIGS. 2 through 13 by an "x" or as a tilted "plus" sign. The predetermined angle in most examples is 180 degrees while in one example (FIGS. 6, 7) it is 45 degrees and in another example (FIGS. 12, 13) 90 degrees.

FIGS. 2 through 13 show six different embodiments of the first jaw member 30 and almost as many different embodiments of the second jaw member 40. The embodiments of the first jaw member 30 and the embodiments of the second jaw member 40 can in part be combined otherwise than as shown in FIGS. 2 through 13. Exceptions arise from various functions, which in some cases are mentioned hereinafter.

Figure 2:
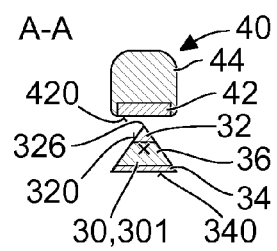
FIG. 2 shows a schematic sectional depiction of jaw members.
Figure 3:
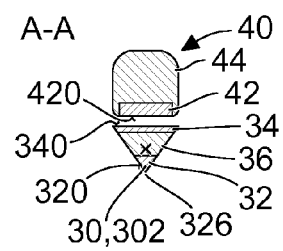
FIG. 3 shows an additional schematic sectional depiction of the jaw members from FIG. 2.

FIGS. 2 and 3 show a first jaw member 30 with an isosceles-triangular cross-section. One corner of the cross-section is configured by a first electrode 32 with a roof-shaped electrode surface 320 and an edge 326. The roof-shaped electrode surface 320, in particular the edge 326, with the first jaw member 30 in the first working position 301 shown in FIG. 2, faces the second jaw member and is turned away from the second jaw member 40 in the second working position 302 shown in FIG. 3.

An opposite side of the cross-section of the first jaw member 30, turned away from the corner of the cross-section formed by the first electrode 32, is formed by a second electrode 34 with an essentially level electrode surface 340. Because the second electrode 34 also forms the two neighboring corners of the triangular cross-section of the first jaw member 30, the electrode surface 340 comprises one edge each on the sides of a large level area and, connected thereto, one narrow strip-shaped region each. The second electrode 34 and the large level area of the electrode surface 340 of the second electrode 34 are turned away from the second jaw member 40 when the first jaw member is in the first working position 301 shown in FIG. 2 and are turned toward the second jaw member 40 when the first jaw member 30 is in the second working position 302 shown in FIG. 3.

The second jaw member 40 shown in FIGS. 2 and 3 includes an electrode 42 with a rectangular cross-section and a level electrode surface 420. In addition, the second jaw member 40 includes an insulation 44 in the form of an insulating body, which surrounds three sides of the cross-section of the electrode 42. Outlying edges of the insulation 44 are rounded. The insulation 44 comprises, for example, an electrically insulating synthetic material, an electrically insulating ceramic or other electrically insulating material.

When the first jaw member 30 is in the first working position 301 shown in FIG. 2, between the roof-shaped electrode surface 320 or the edge 326 on the first jaw member 30 and the opposite level electrode surface 420 on the second jaw member 40, there develops a current density distribution that is dominated by a strong concentration and a pronounced maximum of the amount of the current density in the proximity of the edge 326 on the first jaw member 30.

The roof-shaped electrode area 320 and the edge 326, in interaction with the electrode surface 420 on the second jaw member 40, are suited for mechanically crushing tissue and, under some conditions, severing or cutting it. In this process the current density distribution dictated by the shape of the electrode surfaces 320, 420 causes a relatively small-surface Joulean heating and atrophying of the tissue and can, in addition, support the cutting process.

When the first jaw member 30 is in the second working position 302 shown in FIG. 3, with the essentially level electrode surface 340 of the second electrode 36 of the first jaw member 30 and with the level electrode surface 420 of the electrode 42 of the second jaw member 40, two extended electrode surfaces, which aside from the edges comprise no structure, are situated essentially parallel to one another. A current concentration develops that is essentially homogeneous over a large spatial area, without a distinct maximum or distinct concentration. This current concentration distribution is appropriate for large-scale Joulean heating and atrophying of tissue, such that the tissue is not simultaneously mechanically processed at all or in any case only to a small extent.

Figure 4:
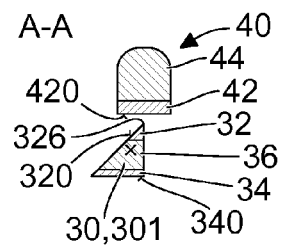
FIG. 4 shows a schematic sectional depiction of additional jaw members.
Figure 5:
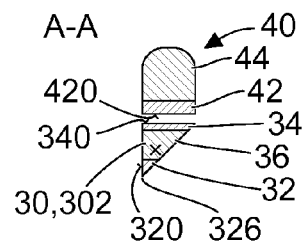
FIG. 5 shows an additional schematic sectional depiction of the jaw members from FIG. 4.

FIGS. 4 and 5 show a first jaw member 30, which, similarly as in the embodiment in FIGS. 2 and 3, has a three-sided but small isosceles-triangular cross-section. Similarly as with the embodiment in FIGS. 2 and 3, when the first jaw member 30 is in the first working position shown in FIG. 4, a strongly localized current density distribution develops with distinct maximum in the vicinity of the edge 326 and, with the first jaw member 30 in the second working position 302 shown in FIG. 5, a large-area, essentially homogeneous current density distribution develops without distinct concentration or distinct maximum. Possible applications correspond to the applications described above with reference to FIGS. 2 and 3.

When the first jaw member 30 is in the first working position 301 shown in FIG. 4, the asymmetrical shape of the roof-shaped electrode surface 320 of the first electrode 32 of the first jaw member 30 can cause an asymmetrical current density distribution. In particular, between the flank of the roof-shaped electrode surface 320 of the first electrode 32 of the first jaw member 30, oriented to the left in FIG. 4, and the electrode 42 of the second jaw member 40, a higher current density can develop than in the opposite spatial area at the right between the flank of the roof-shaped electrode surface 320 of the first electrode 32 of the first jaw member 30, oriented toward the right in FIG. 4, and the electrode surface 420 of the electrode 42 of the second jaw member 40. The embodiment in FIGS. 4 and 5 can therefore be suited to cut through vessels, for example, when the first jaw member 30 is in the first working position 301 shown in FIG. 4, such that one of the two developing vein ends can be more strongly closed up by electrocauterization than the other.

The embodiment in FIGS. 4 and 5 is further distinguished from the embodiment in FIGS. 2 and 3 in that the insulating body that forms the insulation 44 does not surround the electrode 42 of the second jaw member 40 on three sides, but only borders on one side of the electrode 42. The electrode surface 420 of the second jaw member 40 therefore—similarly as the electrode surface 340 of the second electrode 34 of the first jaw member 30 of the embodiment in FIGS. 2 and 3—comprises edges on the borders of a large level area and one narrow stripe-shaped area each bordering on these.

Figure 6:
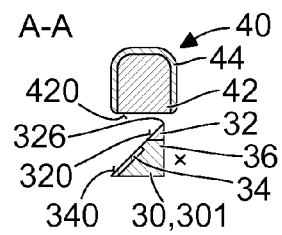
FIG. 6 shows a schematic sectional depiction of additional jaw members.
Figure 7:
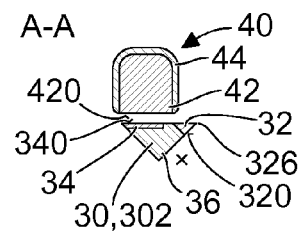
FIG. 7 shows an additional schematic sectional depiction of the jaw members from FIG. 6.

FIGS. 6 and 7 show an embodiment in which the first jaw member 30 comprises an asymmetrically triangular or non-isosceles-triangular cross-section, similarly as in the embodiment in FIGS. 4 and 5. Contrary to the embodiments in FIGS. 2 through 5, in the embodiment in FIGS. 6 and 7 the second electrode 34 is not positioned on the edge of the cross-section that is opposite the corner formed by the first electrode 32, but rather on a side bordering on this corner. One result is that the distance between the electrode surface 320 of the first electrode 32 on the one hand and the electrode surface 340 of the second electrode 34 on the other hand is smaller than in the embodiments in FIGS. 2 through 5. An additional result is that a rotation of only about 45 degrees is situated between the working positions 301, 302 of the first jaw member 30 shown in FIGS. 6 and 7. In an additional working position, which is not illustrated, an addition electrode surface, not shown in FIGS. 6 and 7, can be activated on the first jaw member 30 or can be positioned with respect to the second jaw member 40.

The embodiment in FIGS. 6 and 7 is further distinguished from the embodiments in FIGS. 2 through 5 in that the cross-section of the electrode 42 of the second jaw member 40 comprises an essentially larger surface area and the insulation 44 surrounds the electrode 42 of the second jaw member 40 on three sides in the form of an insulating coating. In particular with the electrode 42 configured of metal, the jaw member 40 can assume a higher bending moment, because of the greater cross-section of the electrode 42, than when the insulation 44 comprises a material with low firmness.

Figure 8:
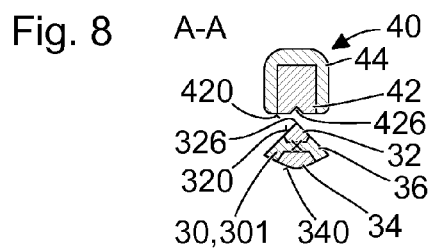
FIG. 8 shows a schematic sectional depiction of additional jaw members.
Figure 9:
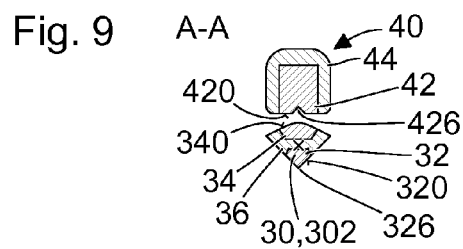
FIG. 9 shows an additional schematic sectional depiction of the jaw members from FIG. 8.

FIGS. 8 and 9 show an embodiment in which the first jaw member has a cross-section with the shape of a deltoid with a rounded corner. A first electrode 32 of the first jaw member 30 forms a roof-shaped electrode surface with an edge 326. A second electrode 34 with a convex arched and smooth electrode surface 340 forms the rounded corner of the cross-section, which is opposite the corner formed by the first electrode 32.

In the example shown in FIGS. 8 and 9, neither the roof-shaped electrode surface 320 of the first electrode 32 nor the curved smooth electrode surface 340 of the second electrode 34 extends to one of the two other corners of the cross-section of the first jaw member 30. These two other corners of the cross-section of the first jaw member 30 are thus formed by the insulation 36 between the electrode surface 32, 34.

The cross-section of the second jaw member 40 of the embodiment in FIGS. 8 and 9 resembles in some respects the embodiments in FIGS. 2 through 7, in particular the embodiment in FIGS. 6 and 7. Contrary to the embodiments in FIGS. 2 through 7, the electrode surface 420 of the electrode 42 of the second jaw member 40 comprises a groove or notch 426 with a V-shaped cross-section.

When the first jaw member 30 is in the first working position 301 shown in FIG. 8, the edge 326 of the first electrode 32 of the first jaw member 30 is situated opposite the groove 426 in the electrode 42 of the second jaw member 40. The electrosurgical instrument can be configured in such a way that the edge 326 on the first jaw member 30 can engage partly or completely in the groove 426 on the second jaw member 40. When the first jaw member 30 is in the second working position 302 shown in FIG. 9, the arched smooth electrode surface 340 of the second electrode 34 of the first jaw member 30 is situated opposite the electrode surface 420 of the electrode 42 of the second jaw member 40.

Similarly as with the embodiments in FIGS. 2 through 7, in the embodiment in FIGS. 8 and 9 the different shapes of the electrode surfaces 320, 340, when the first jaw member 30 is in the first working position 301, cause a strong concentration of the current flow with a distinct maximum of current density in the vicinity of the edge 326 on the first electrode 32 and, when the first jaw member 30 is in the second working position 302, the smooth shape of the electrode surface 340 causes a markedly less concentrated current density distribution. The difference between the current density distributions in the working positions 301, 302 of the first jaw member 30 is, however, smaller in the embodiment in FIGS. 8 and 9 than in the embodiments in FIGS. 2 through 7 because the groove 426 on the electrode 42 of the second jaw member 40 corresponding to the edge 326 on the first electrode 32 of the first jaw member 30 partly counteracts the concentration of current density. In addition, the convex curvature of the electrode surface 340 of the second electrode 34 of the first jaw member 30 and the convex edges on both sides of the groove 426 of the electrode 42 of the second jaw member 40 cause a concentration of current density in its vicinity and thus a markedly less homogeneous current density distribution than with the embodiments in FIGS. 3 through 7 when the first jaw member 30 is in the respective second working position 302.

Figure 10:
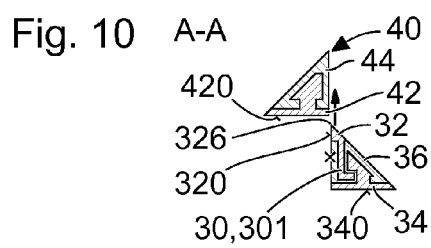
FIG. 10 shows a schematic sectional depiction of additional jaw members.
Figure 11:
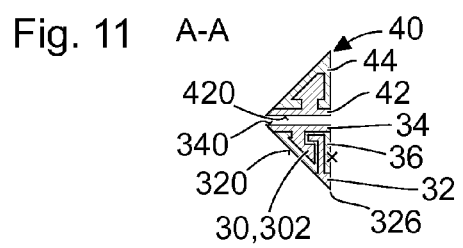
FIG. 11 shows an additional schematic sectional depiction of the jaw members from FIG. 10.

FIGS. 10 and 11 show an embodiment that resembles the embodiments in FIGS. 2 through 9 in some characteristics. In the embodiment in FIGS. 10 and 11, both jaw members 30, 40 have a triangular cross-section. One corner of the triangular cross-section of the first jaw member 30 is formed by a first electrode 32 or its edge 326. The opposite side of the triangular cross-section of the first jaw member 30 is formed by an essentially level electrode surface 340 of a second electrode 34.

Because in the illustrated example the second electrode 34 forms the entire side of the triangular cross-section of the first jaw member 30, the electrode surface 340 comprises one side each on the edges of a large level area and two narrow strip-shaped areas adjoining these that extended into the neighboring sides. An insulation, whose spatial shape is discussed below, is positioned between the electrodes 34, 35 of the first jaw member 30.

The second jaw member 40 comprises on its side facing the first jaw member 30 an electrode 42 with an essentially level electrode surface 420. Because the electrode 42 extends over the entire side of the triangular cross-section of the second jaw member 40, the electrode surface 420 comprises one side each on two opposite edges of a large flat area, and connected on it a narrow strip-shaped area that extends into the particular adjoining side of the triangular cross-section. Apart from these narrow strip-shaped areas of the electrode surface 420, two sides of the triangular cross-section of the second jaw member 40 are formed by an insulation 44.

With the first jaw member 30 in the first working position 301 shown in FIG. 10, the roof-shaped electrode surface 320, in particular its edge 326, is situated opposite the first electrode 32 of the first jaw member 30 and an edge of the essentially level electrode surface 420 is situated opposite the electrode 42 of the second jaw member 40. The first jaw member 30, corresponding to an arrow shown in FIG. 10, can be moved past the second jaw member 40 in order to sever tissue mechanically by shearing.

With the first jaw member 30 in the second working position 302 shown in FIG. 11, the essentially level electrode surface 340 of the second electrode 34 of the first jaw member 30 and the essentially level electrode surface 420 of the electrode 42 of the second jaw member 40 are situated parallel or essentially parallel to one another.

The current density distributions caused when the first jaw member 30 is in the two working positions correspond approximately to the current density distributions with the embodiments in FIGS. 2 through 7, in particular the current density distributions with the embodiment in FIGS. 4 and 5.

With the embodiments in FIGS. 2 through 9, the electrodes 32, 34 or 42 and the insulation 36 or 44, configured as an insulation body or insulation layer, are each joined, in particular, in a firm bonding. In FIGS. 10 and 11, cross-sections of the electrodes 32, 34, 42 as well as of the insulations 36, 44 with undercuttings can be recognized. This allows a form-locking connection as an alternative or in addition to the firm binding.

Figure 12:
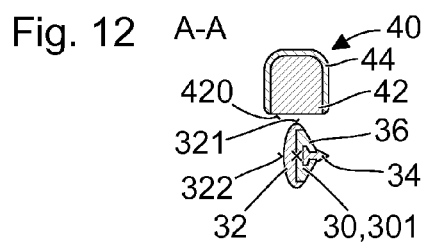
FIG. 12 shows a schematic sectional depiction of additional jaw members.
Figure 13:
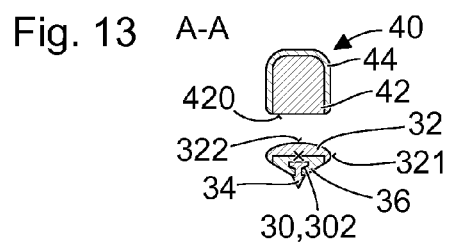
FIG. 13 shows an additional schematic sectional depiction of the jaw members from FIG. 12.

FIGS. 12 and 13 show an embodiment that resembles in some characteristics the embodiments in FIGS. 2 through 11. In particular, the second jaw member 40 resembles the second jaw member of the embodiment in FIGS. 6 and 7.

Contrary to the embodiments in FIGS. 2 through 11, the first jaw member 30 in the embodiment in FIGS. 12 and 13 has a cross-section with a border with an elliptical portion. The elliptical portion of the border of the cross-section of the first jaw member 30 is formed by an electrode surface 320 of a first electrode 32 of the first jaw member 30.

With the first jaw member 30 in the first working position 301 shown in FIG. 12, a strongly curved first electrode area 321 of the electrode surface 320 of the first electrode 32 is situated close to a focal point of the ellipse opposite the second jaw member 40. With the first jaw member 30 in the second working position 302 shown in FIG. 13, a weakly curved second electrode area 322 of the electrode surface 320 of the first electrode 32 of the first jaw member 30 is situated opposite the second jaw member 40. As a result, with the first jaw member 30 in the working positions 301, 302, various current density distributions develop between the electrode 32 of the first jaw member 30 and the electrode 42 of the second jaw member 40. With the first jaw member 30 in the first working position 301 shown in FIG. 12, the current flow is more strongly localized or the current density distribution has a more pronounced maximum than when the first jaw member 30 is in the second working position 302 shown in FIG. 13.

Because of the continually varying curvature of the electrode surface 320 of the first electrode 32 on the first jaw member 30, when the first jaw member 30 is in other positions between the working positions 301, 302 shown in FIGS. 12 and 13, current density distributions can be generated that lie between those of the working positions 301, 302.

The first jaw member 30 further comprises a second electrode 34 having an electrode surface 340 with an edge. In an additional working position, which is not shown in FIGS. 12 and 13 and which is turned 180 degrees away from the second working position 302 shown in FIG. 13, the electrode surface 340 and the edge of the second electrode 34 of the first jaw member 30 are situated opposite the electrode surface 420 of the electrode 42 of the second jaw member 40. Here a current density distribution can develop that resembles the current density distributions in the embodiments in FIGS. 2 through 7, with the first jaw member 30 in the first working position 301 in each case. The edge of the second electrode 34 of the first jaw member 30 can also be configured for mechanical cutting.

Figure 14:
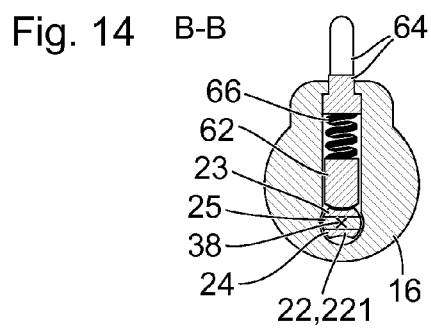
FIG. 14 shows a schematic sectional depiction of the instrument from FIG. 1.
Figure 15:
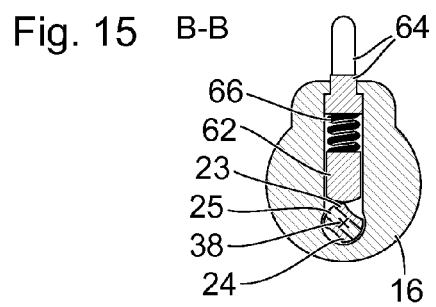
FIG. 15 shows an additional schematic sectional depiction of the instrument from FIGS. 1 and 14.

FIGS. 14 and 15 show schematic sectional depictions of the electrosurgical instrument 10 from FIG. 1 along the plane B-B indicated in FIG. 1 perpendicular to the plane of projection of FIG. 1. In the proximal end 16 of the shaft 15 or of the electrosurgical instrument 10, the axle 22 is mounted to rotate around the rotation axis 38. The axle 22 includes a first electrically conductive area 23, a second electrically conductive area 24 and an insulation area 25 that is positioned between the electrically conductive areas 23, 24 and that electrically insulates the electrically conductive areas 23, 24 from one another. The first electrically conductive area 23 of the axle 22 is in an electrically conductive connection with the first electrode 32 of the first jaw member 30 (see also FIGS. 2 through 13), and is in particular of one-piece configuration. The second electrically conductive area 24 of the axle 22 is in an electrically conductive connection with the second electrode 34 of the first jaw member 30, and is in particular of one-piece configuration. The insulation area 25 of the axle 22 can be configured as a single unit with the insulation 36 of the first jaw member 30.

The axle 22 has a cross-section with a contour that is circular in portions. At two positions opposite one another, the contour of the cross-section of the axle 22 departs from circular shape. In particular, each electrically conductive area 23, 24 of the axle 22 comprises a concave surface portion.

The electrosurgical instrument comprises a sliding contact 62, a plug-in contact 64 and a pressure spring between the sliding contact 62 and the plug-in contact 64. The sliding contact 62 is mounted slidably in the proximal end 16 of the shaft, in a direction parallel to the sectional plane B-B and perpendicular to the rotation axis 38. The plug-in contact 64 is fastened rigidly in the proximal end 16, for example joined in form-locked and/or firmly bonded connection. An end of the plug-in contact 64 that protrudes from the electrosurgical instrument is configured for electrically conductive connection with a plug-in connector of an electric cable. For this purpose, the plug-in contact 64 comprises, in particular, a slit that in FIGS. 14 and 15 is parallel to the sectional plane B-B (see also FIG. 1). The slit makes spring-elasticity of the plug-in contact 64 possible.

A pressure spring 66 in the form of a coil spring or other electrically conductive elastic element is positioned between the plug-in contact 64 and the sliding contact 62. The pressure spring 66 forms an electrically conductive connection between the plug-in contact 64 and the sliding contact 62. In addition, the pressure spring 66 presses the sliding contact 62 against the axle 22. With the axle 22 in the position shown in FIG. 14, the sliding contact 62 is situated in an indentation of the first electrically conductive area 23. Thus an electrically conductive connection is established between the plug-in contact 64 and the first electrode 32 of the first jaw member 30. By form-locking between the sliding contact 62 and the indentation in the first electrically conductive area 23 of the axle 22, the axle 22 is held in the first working position 221 shown in FIG. 14. By rotating the axle 22 out of the first working position 221, for example into the position shown in FIG. 15, the sliding contact 62 is slid against the force of the pressure spring 66. This requires a minimum torque, which can be generated, for example, manually on the rotation wheel 58 (see also FIG. 1).

In the embodiment presented with reference to FIGS. 14 and 15, the sliding contact 62 and pressure spring 66 fulfill two functions simultaneously, namely electrical contacting and catch-locking. Alternatively, it is possible to realize both functions by means of partly or completely separate devices.

The pivotable part 54 of the handling device 50 is only implied in FIG. 1. FIGS. 16 and 17 show schematic and somewhat more detailed depictions of an embodiment of a pivotable part 54 of a handling device. Thus FIG. 16 shows a section along a plane C-C perpendicular to the rotation axis 38 (see also FIG. 1) and parallel to the planes A-A and B-B, and FIG. 17 shows a section along a plane D-D perpendicular to the plane C-C and parallel to the plane of projection of FIG. 1. The plane D-D is indicated in FIG. 16, and the plane C-C in FIG. 17.

The pivotable part 54 of the handling device has a Y-shaped form and is mounted so that it can pivot around a pivot axis 548 by means of an axle 546. The pivotable part 54 is mounted so that it can rotate in relation to the axle 546 and on it, and/or the axle 546 is rotatably mounted in the electrosurgical instrument 10. Two ends of the pivotable part 54 are connected by an axle 28 on which the proximal end of the pull rod 27 is mounted. The pull rod 27 is mounted to rotate around a pivot axis 29 in relation to the pivotable part 54 of the handling device. The axle 28 can rotate in relation to the pivotable part 54 of the handling device, and/or the pull rod 27 is rotatable in relation to the axle 28.

The axle 28 and the two legs of the pivotable part 54 of the handling device circumscribe a space in which the axle 22, consisting of two electrically conductive areas 23, 24 separated by an insulation area 25, is positioned and in which it can rotate around the rotation axis 38. The pivotable part 54 of the handling device can pivot within a predetermined angle area, as already explained above with reference to FIG. 1. On the basis of the coupling of the pull rod 27 with the pivotable part 54 of the handling device by means of the axle 28, every pivot movement of the pivotable part 54 of the handling device causes a sliding of the pull rod 27 and vice versa.

FIG. 18 shows a schematic depiction of an alternative embodiment of the pivotable part 54 of a handling device, which resembles in some characteristics the pivotable part 54 from FIGS. 16 and 17. Here FIG. 18 shows a section along a plane C-C perpendicular to the rotation axis 38 (see also FIG. 1) and parallel to the planes A-A and B-B. A section along the plane D-D indicated in FIG. 18, perpendicular to the plane C-C and parallel to the plane of projection of FIG. 1, is similar enough to the section shown in FIG. 17 so that this section is not illustrated separately.

The embodiment of the pivotable part 54 of the handling device shown in FIG. 18 is distinguished from the pivotable part presented above with reference to FIGS. 16 and 17 in particular in that instead of a Y-shaped form it is approximately L-shaped. In addition, the pull rod 27 is mounted to rotate on a bolt-shaped area 548 of the pivotable part 54.

The shape of the pivotable part 54 described with reference to FIG. 18 can require less construction space than the shape presented with reference to FIGS. 16 and 17. In addition, it can be possible to laterally remove the axle 22 and/or the pivotable part 54 of the handling device by a sliding movement parallel to the plane C-C.

Figure 19:
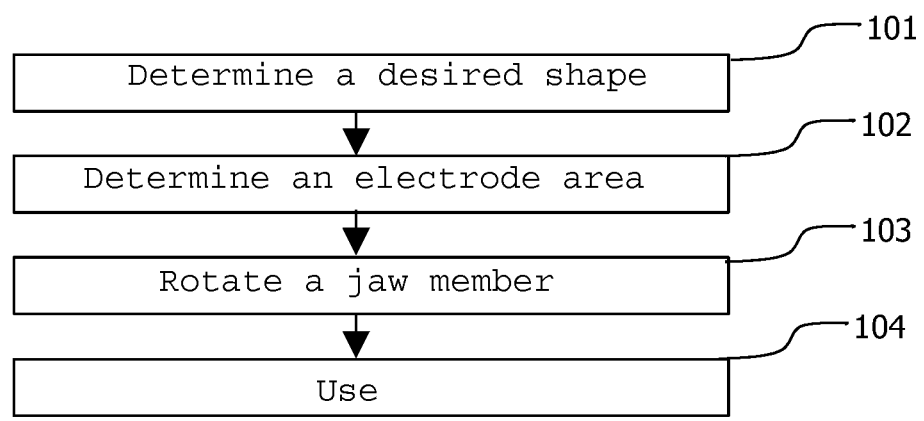
FIG. 19 shows a schematic flow diagram.

FIG. 19 shows a schematic flow diagram of a method, in the framework of which it is possible to perform an electrosurgical procedure and in which it is possible to use an electrosurgical instrument as is described above with reference to FIGS. 1 through 18.

Although the method can also be performed with electrosurgical instruments that differ from the embodiments presented above with reference to FIGS. 1 through 18, reference numbers from FIGS. 1 through 18 are used below by way of example for the sake of simplicity.

In a first step 101, a desired shape of an electrode surface, which is to be inserted during an electrosurgical procedure that is to be performed subsequently, is determined by medical staff, in particular by a physician. The first step 101 can be based on considerations concerning undesired current density distribution and/or concerning practical experience and can depend on whether, for example, tissue of large or small scope is merely to be atrophied or simultaneously is to be cut. The decision on the desired shape of the electrode can also depend on the desired therapeutic outcome and on the type of tissue.

A second step 102 determines which electrode area 320, 321, 322, 340 on a rotatable first jaw member 30 comes closes to the desired shape. In particular, it is determined here whether the shape of a first electrode area 320, 321 or the shape of a second electrode area 322, 340 on a rotatable first jaw member 30 is more similar to the desired shape. In addition, the second step 102, or the decision made in it, is taken as a rule by the same medical staff as the first step 101. However, the second step 102, contrary to the first step, contains no considerations based directly on therapeutic actions and their configuration, or any other specialized medical considerations.

In a third step 103, the first jaw member 30 is rotated into a first predetermined working position 301, in which a first electrode area 320; 321 of the first jaw member 30 is facing a second jaw member 40, or into a second predetermined working position 302, in which a second electrode area 340, 322 of the first jaw member 30 is facing the second jaw member 40. Whether the first jaw member 30 is rotated into the first predetermined working position 301 or into the second predetermined working position 302 depends in particular on the outcome of the second step 102. In addition, the jaw member 30 can be rotated into a third or additional predetermined working position.

The third step 103 constitutes a preparation of an electrosurgical procedure, in particular of an electrosurgical instrument that is to be used in that process. The third step 103 itself does not constitute either a surgical or a therapeutic action. In a wider sense, the first step 101 and in particular the second step 102 can also be considered part of the preparation for the electrosurgical procedure. However, preparation of the electrosurgical instrument 10 occurs exclusively in the third step 103.

In a fourth step 104, the electrosurgical instrument 10 that has been prepared in the third step 103 is used to conduct the planned electrosurgical procedure. Only the fourth step 104 constitutes a surgical and possibly also therapeutic step.

What is claimed is:

1. An electrosurgical instrument, having:
a first jaw part with a first electrode area and a second electrode area;
a second jaw part,
wherein at least either the first jaw part or the second jaw part is pivotable about a pivot axis, such that the first and second jaw parts can be moved towards each other or away from each other, wherein the first jaw part is rotatable, relative to the second jaw part, about a rotation axis between a first predetermined working position and a second predetermined working position, wherein in the first predetermined working position the first electrode area of the first jaw part faces towards the second jaw part, and wherein in the second predetermined working position the second electrode area of the first jaw part faces towards the second jaw part, wherein the first electrode area is formed by a first electrode, and the second electrode area is formed by a second electrode, characterized in that the first electrode and the second electrode are electrically insulated from each other, and also having:

an electrical contact device for electrically contacting only the first electrode when the first jaw part is located in the first predetermined working position such that the second electrode is electrically isolated from the electrical contact device, and for electrically contacting only the second electrode when the first jaw part is located in the second predetermined working position such that the first electrode is electrically isolated from the electrical contact device.

2. The electrosurgical instrument according to claim 1, in which the first electrode area has a stronger curvature than the second electrode area.

3. The electrosurgical instrument according to claim 1, in which the second jaw part has an electrode area, which faces towards the first jaw part.

4. The electrosurgical instrument according to claim 1, also having:

a shank, on a distal end of which the first and second jaw parts are arranged;

a handling device with a rotation device at a proximal end of the shank, wherein the rotation device is designed for manual actuation;

a transmission device, which mechanically couples the rotation device to the first jaw part, for transmitting at least either a torque or a force from the rotation device to the first jaw part in order to rotate the first jaw part between the first predetermined working position and the second predetermined working position.

5. The electrosurgical instrument according to claim 4, in which the first jaw part is removable from the shank in a distal direction together with the transmission device.

6. The electrosurgical instrument according to claim 1, wherein the electrosurgical instrument is designed such that the first jaw part is adapted to be detachable in a distal direction.

7. The electrosurgical instrument according to claim 1, in which at least either the first electrode area of the first jaw part or the second electrode area of the first jaw part, or a surface area of the second jaw part facing towards the first jaw part, is concave in a longitudinal direction in a vicinity of the pivot axis.

8. The electrosurgical instrument according to claim 6, further comprising a catch-lock to prevent the first jaw part from being detached.

9. The electrosurgical instrument according to claim 1, further comprising a catch-lock to prevent undesired rotation of the first jaw part.

10. The electrosurgical instrument according to claim 1, further comprising a power drive to rotate the first jaw part.

* * * * *